(12) United States Patent
Chen

(10) Patent No.: US 7,104,970 B2
(45) Date of Patent: Sep. 12, 2006

(54) INJECTION SYRINGE WITH SEAL STRUCTURE

(76) Inventor: Long Hsiung Chen, 1F & 2F, No. 2-1, Lane 22, Szu Wei Road, Taipei (TW)

( * ) Notice: Subject to any disclaimer, the term of this patent is extended or adjusted under 35 U.S.C. 154(b) by 413 days.

(21) Appl. No.: 10/627,653

(22) Filed: Jul. 28, 2003

(65) Prior Publication Data

US 2004/0230163 A1 Nov. 18, 2004

(30) Foreign Application Priority Data

May 15, 2003 (TW) .............................. 92208879 U

(51) Int. Cl.
*A61M 5/00* (2006.01)
(52) U.S. Cl. .................... 604/110; 604/111; 604/187
(58) Field of Classification Search ............... 604/110, 604/263, 164, 197, 198, 180–193, 171, 177, 604/240, 17, 85–90; 128/919
See application file for complete search history.

(56) References Cited

U.S. PATENT DOCUMENTS

| 4,391,273 A | * | 7/1983 | Chiquiar-Arias ............ 604/110 |
| 5,336,198 A | * | 8/1994 | Silver et al. ................. 604/195 |
| 6,117,107 A | * | 9/2000 | Chen ........................... 604/110 |
| 6,413,236 B1 | * | 7/2002 | Van Dyke .................... 604/110 |

* cited by examiner

*Primary Examiner*—Nicholas D. Lucchesi
*Assistant Examiner*—Aamer S. Ahmed
(74) *Attorney, Agent, or Firm*—Rosenberg, Klein & Lee

(57) ABSTRACT

An injection syringe of the present invention comprises a hollow barrel, a needle seat and a plunger. The top of hollow barrel comprises an axial extension which has an upper channel and a lower channel for forming a positioning spring and a seal spring. The inside of the barrel where it is coupled to the axial extension has at lest one piercer. The needle seat is placed in the hollow barrel, and bottom radius of a body of the needle seat is larger than the top of the body for tightly fastening with the seal spring. The top of needle seat has a needle head seat which includes a plurality of positioning sheets thereon and the needle seat is positioned inside the axial extension by a channel of the needle head seat.

10 Claims, 10 Drawing Sheets

US 7,104,970 B2

INJECTION SYRINGE WITH SEAL STRUCTURE

BACKGROUND OF THE INVENTION

1. Field of the Invention

The present invention relates to an injection syringe, more particularly, to an injection syringe with a seal structure which provides a complete seal structure in the injection syringe.

2. Description of the Related Art

Presently, many medical personnel are afflicted with diseases such as AIDS or infection, due to a needle stick which can result in death. The needle stick is a common professional injury and occurs often. According to research, 98% of medical personnel and 70% of doctors feel the potential danger of being stuck by a needle. Although the injury of needle stick is not serious, the injury can lead to the death of a person. After using the injection needle with the blood of the patient, the operators could become infected if they are stuck by the needle.

The needle stick can occur at a patient's bedside or other places such as an operating room, intensive care unit, treatment room and emergency room. A needle can easily injure medical personnel when the needle cap is not placed on the needle after use. Some research is focused to eliminate the operation of placing a cap back on the needle for avoiding being stuck by the needle.

Further, the injection syringe of the present invention has many advantages such as the coupling area between the barrel and the axial extension has at least one piercer. Furthermore, the needle seat is placed in the hollow barrel, and a bottom radius of a body of the needle seat is larger than the top of the body for tightly fastening with a seal spring. Additionally, the top of needle seat has a needle head seat which includes a plurality of positioning sheets, and the needle seat is positioned on the axial extension by a channel of the needle head seat.

The top of a plunger has a fastening seat which comprises a cylindrical column. An inclined surface of the cylindrical column comprises a plurality of flukes for coupling to a bulge loop on the needle seat. The top of fastening seat has a piston which includes a hole for passing the cylindrical column. And, the top of plunger has an opening to couple to the fastening seat and to easily break the plunger after using the syringe.

It is to be understood that both the foregoing general description and the following detailed description are exemplary, and are intended to provide further explanation of the invention as claimed.

BRIEF DESCRIPTION OF THE DRAWINGS

The accompanying drawing is included to provide a further understanding of the invention, and is incorporated in and constitutes a part of this specification. The drawing illustrates an embodiment of the invention and, together with the description, serves to explain the principles of the invention. In the drawing.

DETAILED DESCRIPTION OF THE PREFERRED EMBODIMENTS

Figure 1:
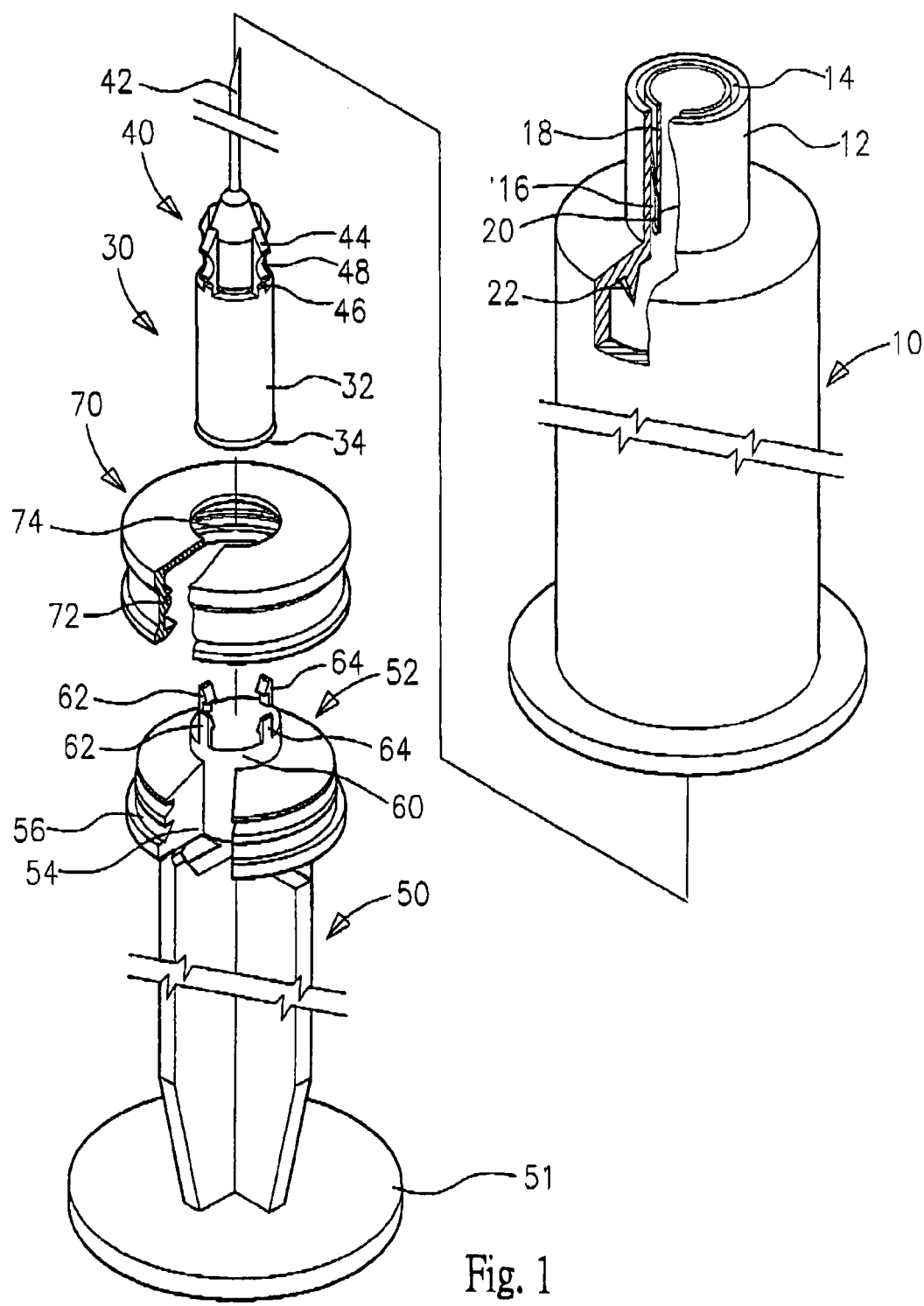
FIG. 1 is an explosive view showing the syringe with seal structure of the present invention.

Reference will now be made in detail to the preferred embodiments of the present invention, examples of which are illustrated in the accompanying drawings. Wherever possible, the same reference numbers are used in the drawings and the description to refer to the same or like parts.

Figure 2:
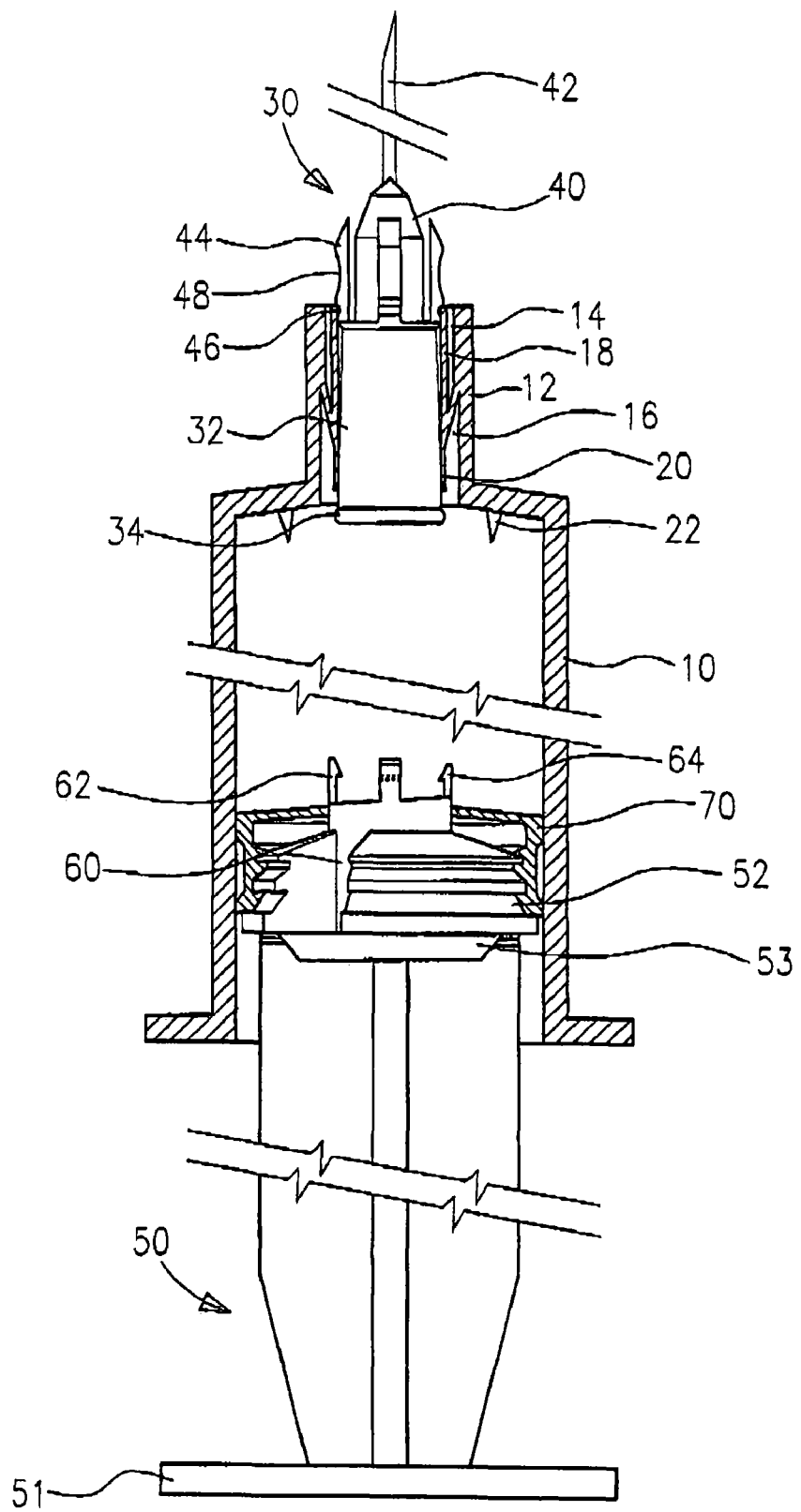
FIG. 2 is a sectional view showing the syringe with seal structure of the present invention.
Figure 3:
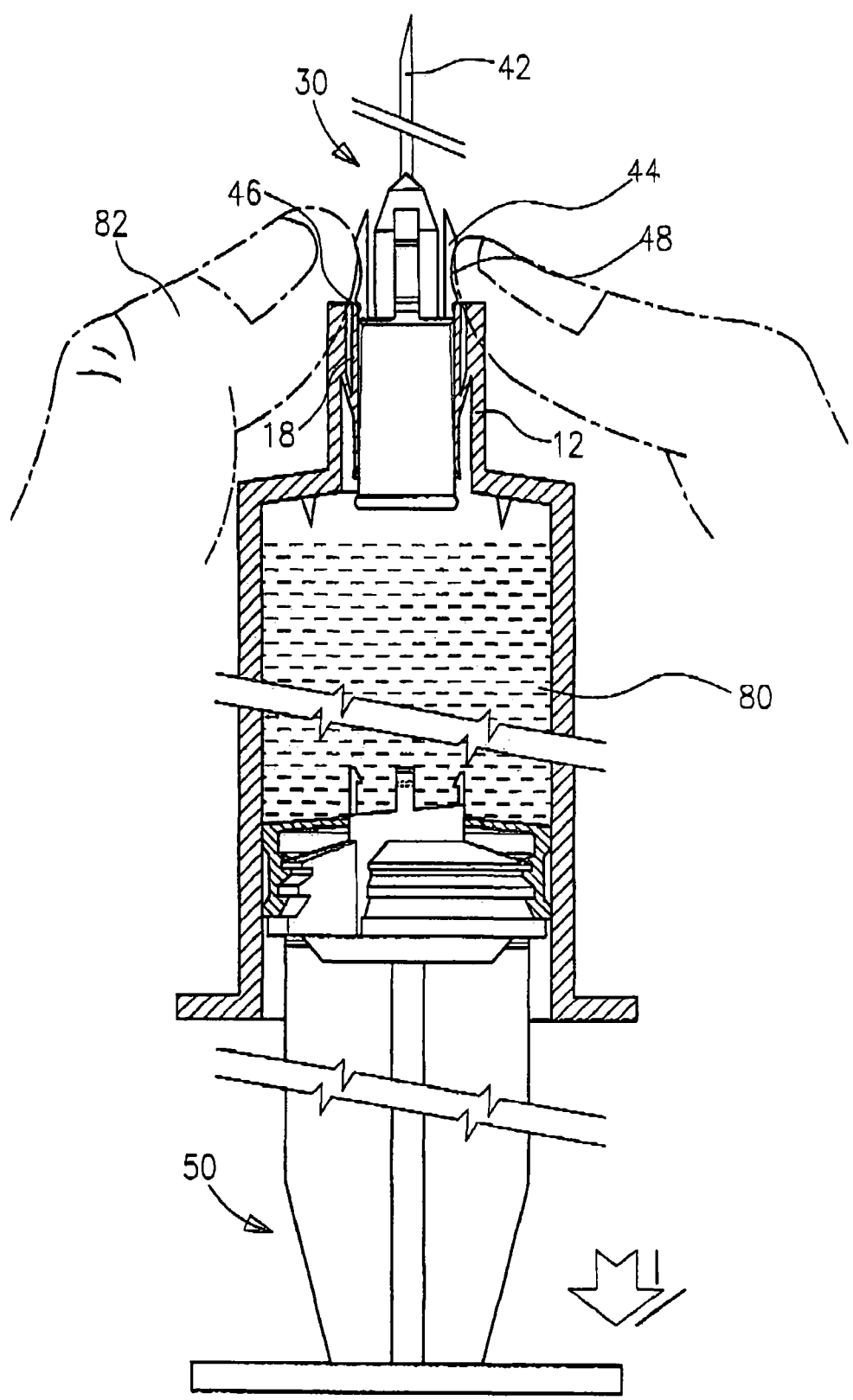
FIGS. 3 to 10 are schematic diagrams showing operation of the syringe with seal structure of the present invention.

Referring to FIGS. 1 and 2, the injection syringe of the present invention comprises a hollow barrel 10 which has an axial extension 12 at the top wherein the inside of axial extension 12 comprises an upper channel 14 and a lower channel 16 defining a positioning spring 18 and a seal spring 20. The point of connection between the barrel 10 and extension 12 includes at least one piercing element 22 projecting inside the barrel 10. The needle seat 30 is placed in the extension 12 and comprises a body 32. The radius of the bottom of body 32 is larger than the top of the body 32 for tightly coupling to the seal spring 20. The seal spring 20 has a spring property so that the seal of barrel 10 has an excellent seal property. The bottom of body 32 has a bulge loop 34, and the top of body 32 has a needle head seat 40 which has a needle 42. The outside of needle seat 40 has a plurality of positioning sheets 44, and each seat 44 has a channel 46. When the needle seat 30 is placed in the extension 12, the channel 46 couples to the positioning spring 18 for fastening the needle seat 30 in the extension 12. Each positioning sheet 44 at the upper of channel 46 of seat 40 further includes a pressing channel 48.

A plunger 50 is placed in the barrel 10, and comprises a flange 51 at the bottom. The top of plunger 50 has a fastening seat 52 and an opening 53. The plunger 50 is coupled to the fastening seat 52. The fastening seat 52 has an axial channel 54 at the outside and a piston 70. The piston 70 is coupled to the fastening seat 52 by a plurality of fastening channels 56, located on an outside of seat 52, coupled to a plurality of bulge rings, positioned on an inside of the piston 70. The piston 70 has a hole 74 for passing a cylindrical column 60 of seat 52 and an inclined surface at the top. The top of inclined surface has a plurality of flukes positioned opposite with respect to each other for example: the first fluke 62 is opposite to a second fluke 64 and the first fluke 62 is taller than the second fluke 64.

Referring to FIGS. 3 to 9, firstly, the needle 42 pierces the cap of medical bottle and a user pulls the plunger 50 back to draw the medical liquid 80 into the hollow barrel 10. Further, the needle seat 30 must be removed from the injection syringe after drawing up the liquid 80 to allow for a new needle seat thereby avoiding a cap remaining on the needle 42 when the needle 42 sticks the cap of medical bottle. Therefore a user presses the pressing channel 48 at the upper end of the sheets 44 to remove the needle seat 30 and places a new needle seat 30 in the extension 12. When the needle seat 30 couples to the extension 12, the channel 46 at the upper end of sheets 22 is coupled to the positioning spring 18.

Figure 4:
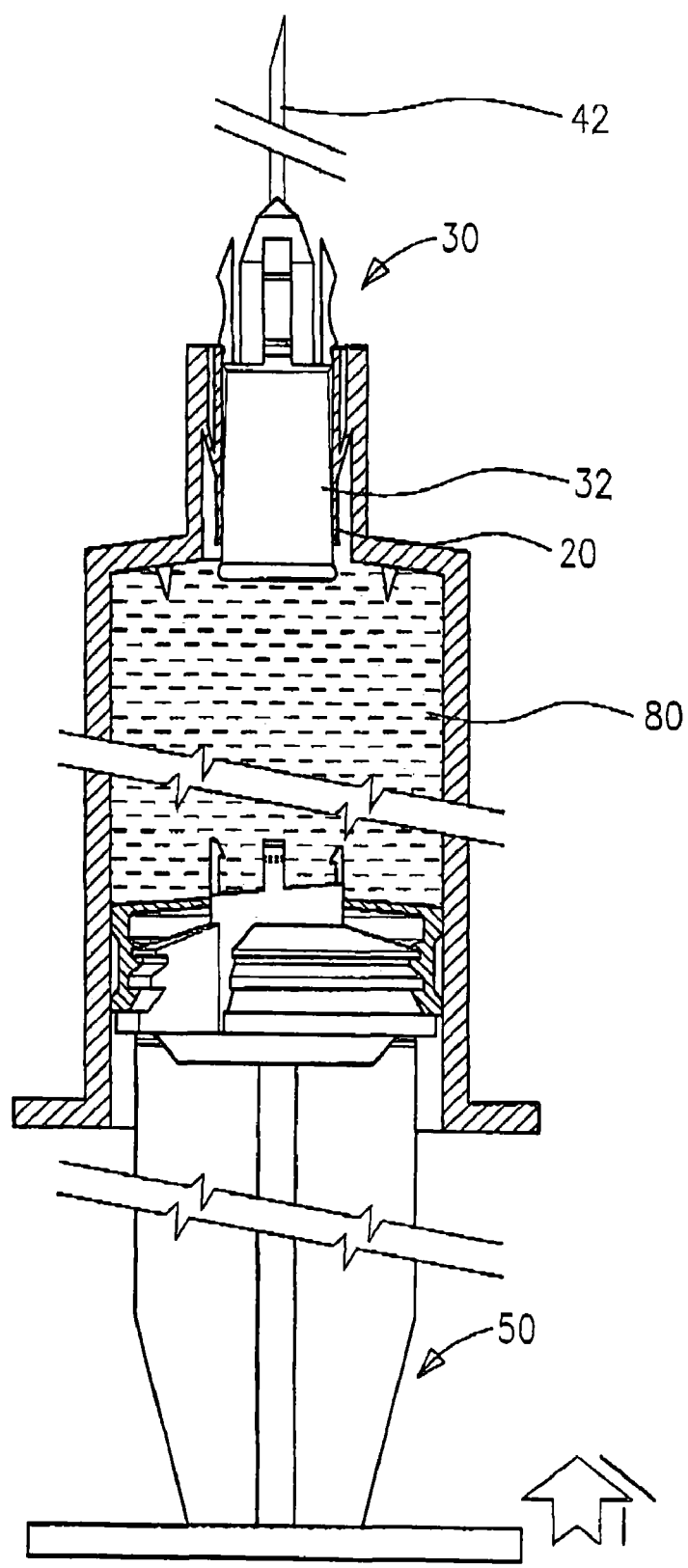

Referring to FIG. 4, displacing the plunger 50 towards the extension 12 causes medical liquid 80 to leave the barrel 10. Since the bottom radius of body 32 is larger than the top of the body 32, a tight coupling is formed with the body 32 thereby giving the seal spring 20 the barrel 10 excellent seal property, and preventing leakage of medical liquid 80.

Figure 5:
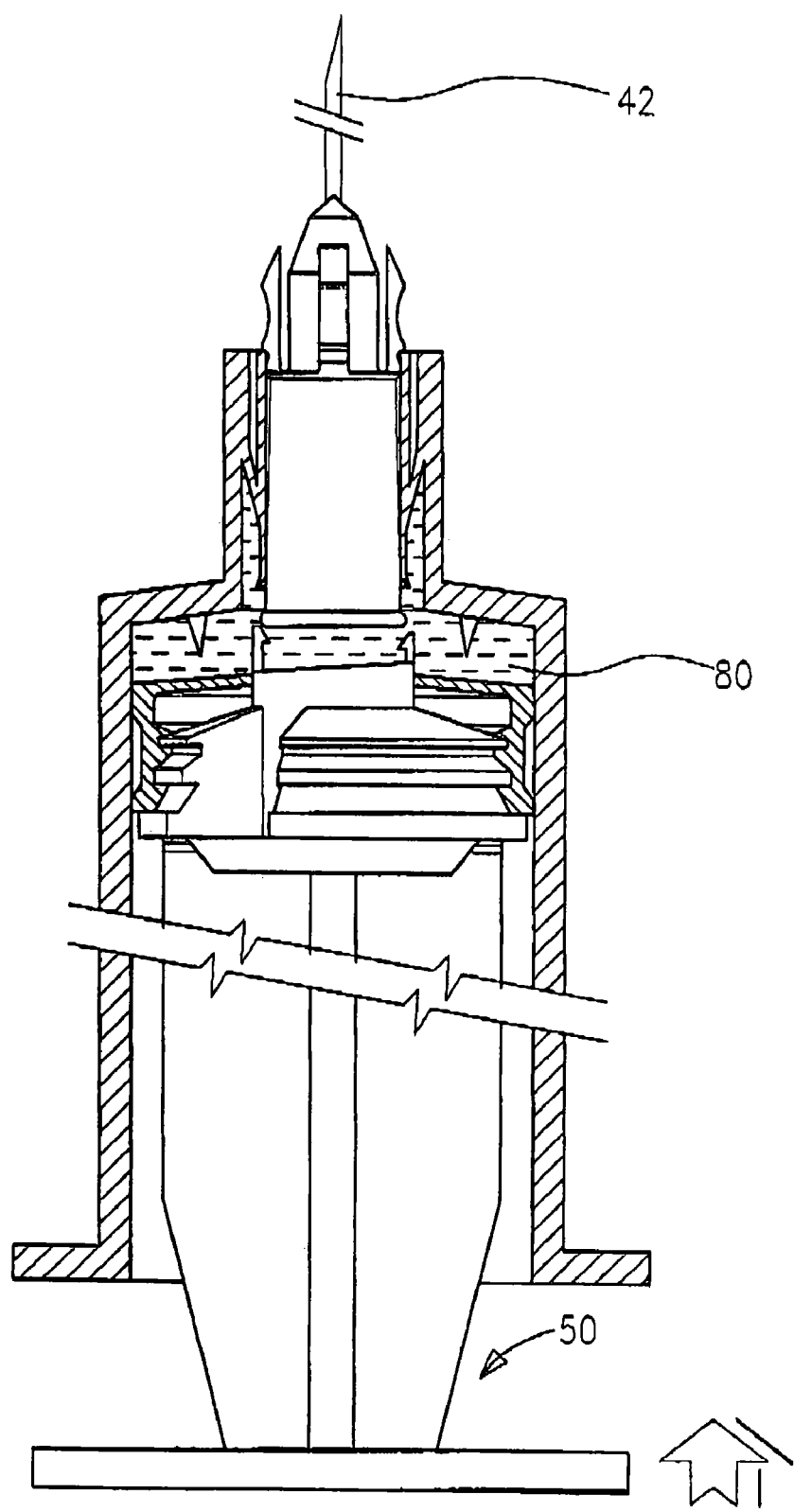

Referring to FIG. 5, displacing the plunger 50 towards the extension 12 causes the medical liquid 80 to be injected into the human body.

Figure 6:
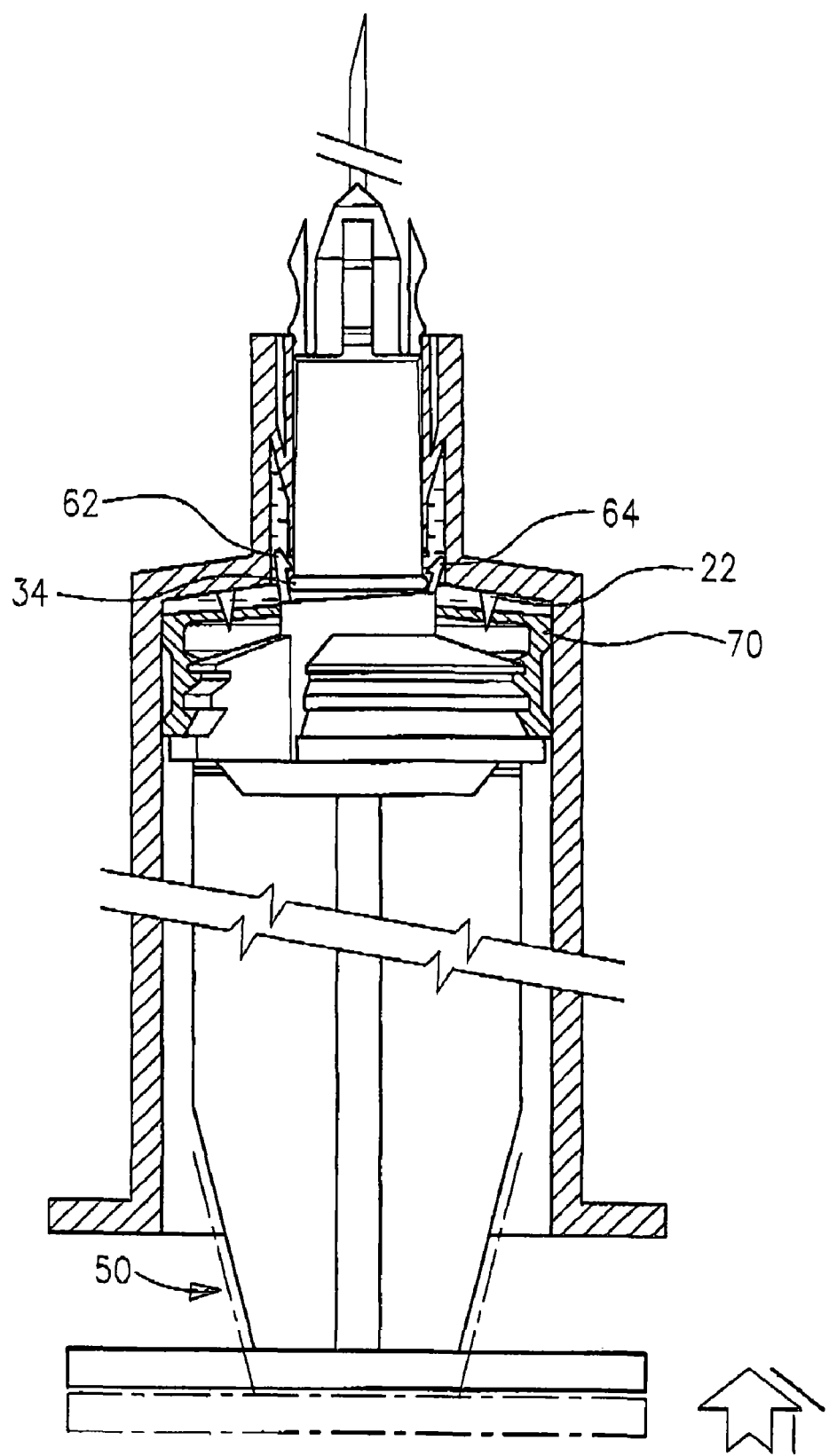
Figure 7:
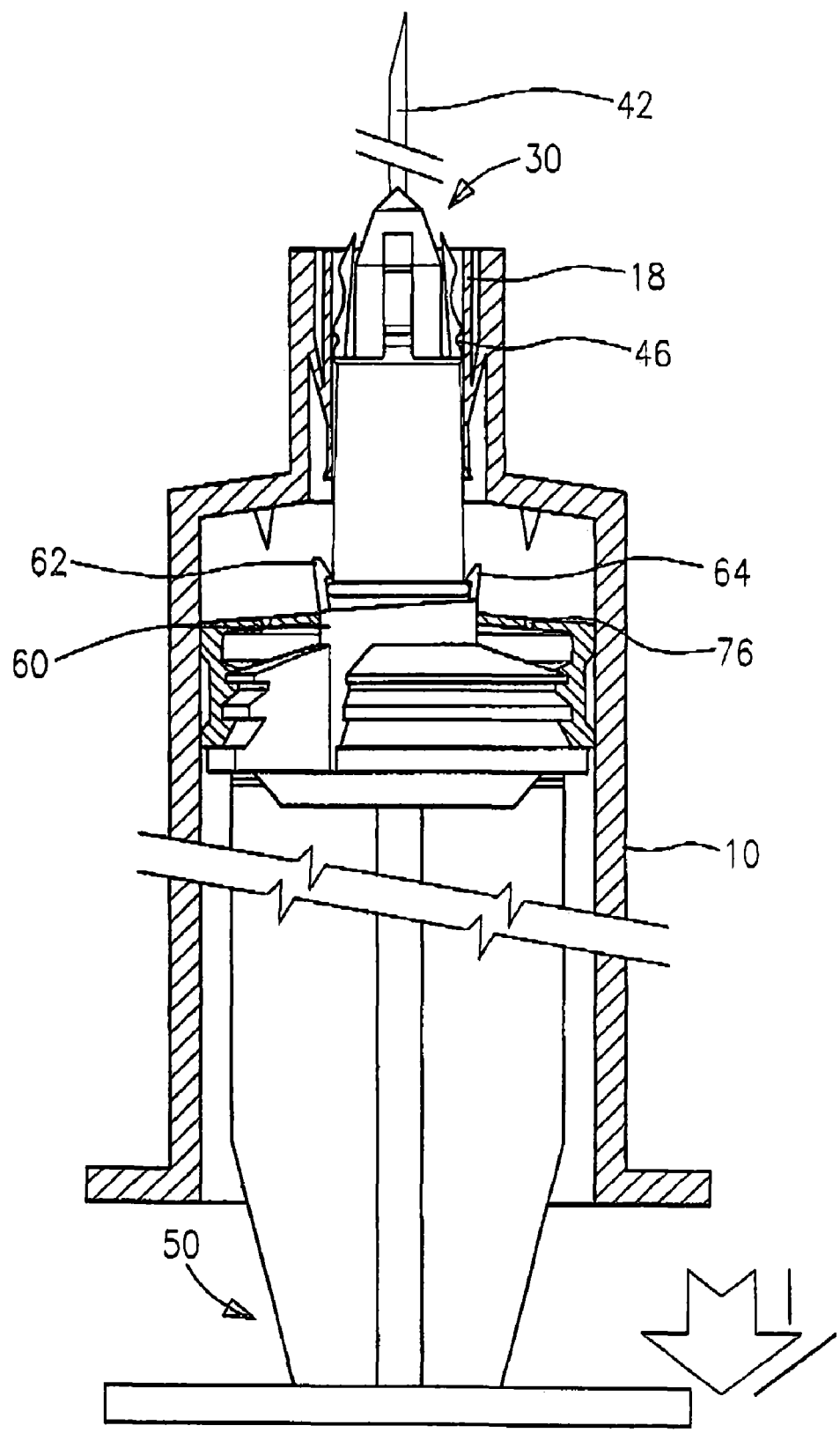
Figure 8:
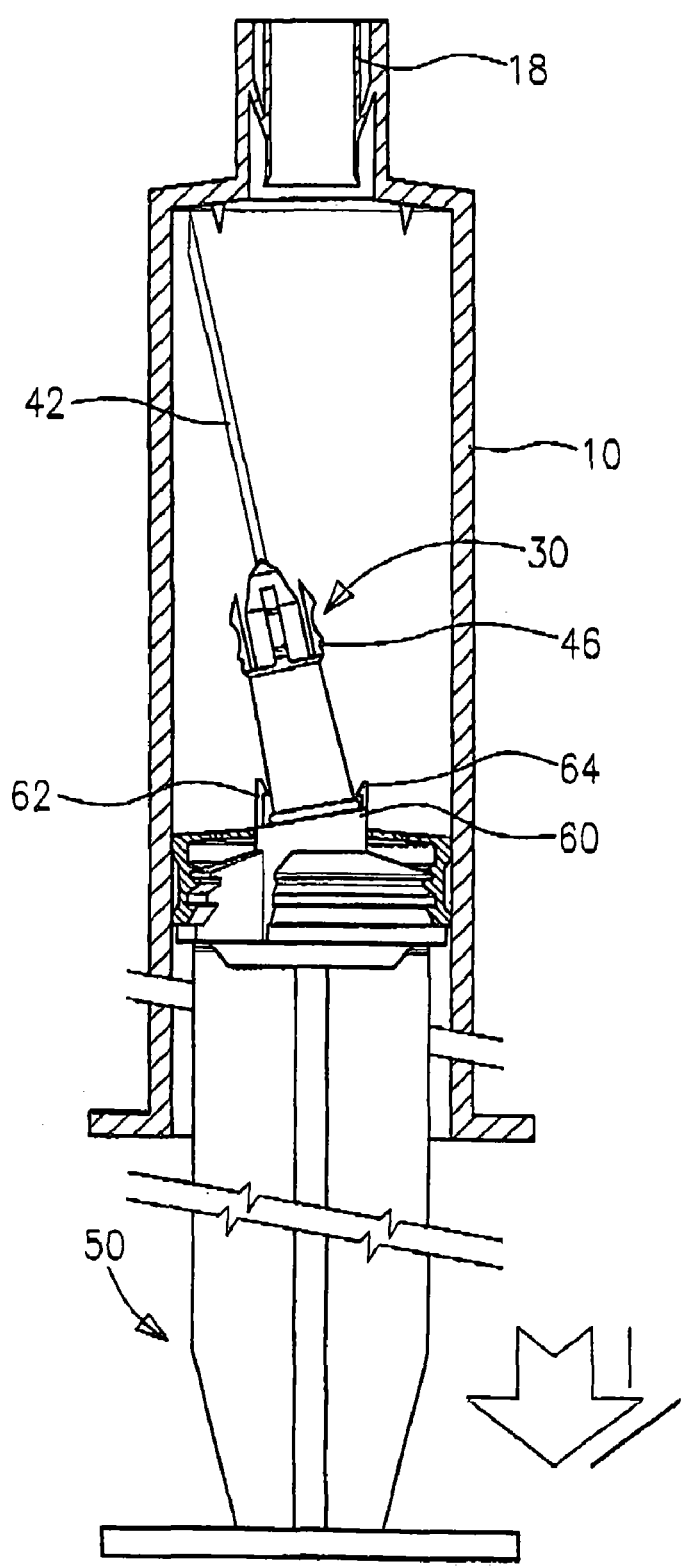
Figure 9:
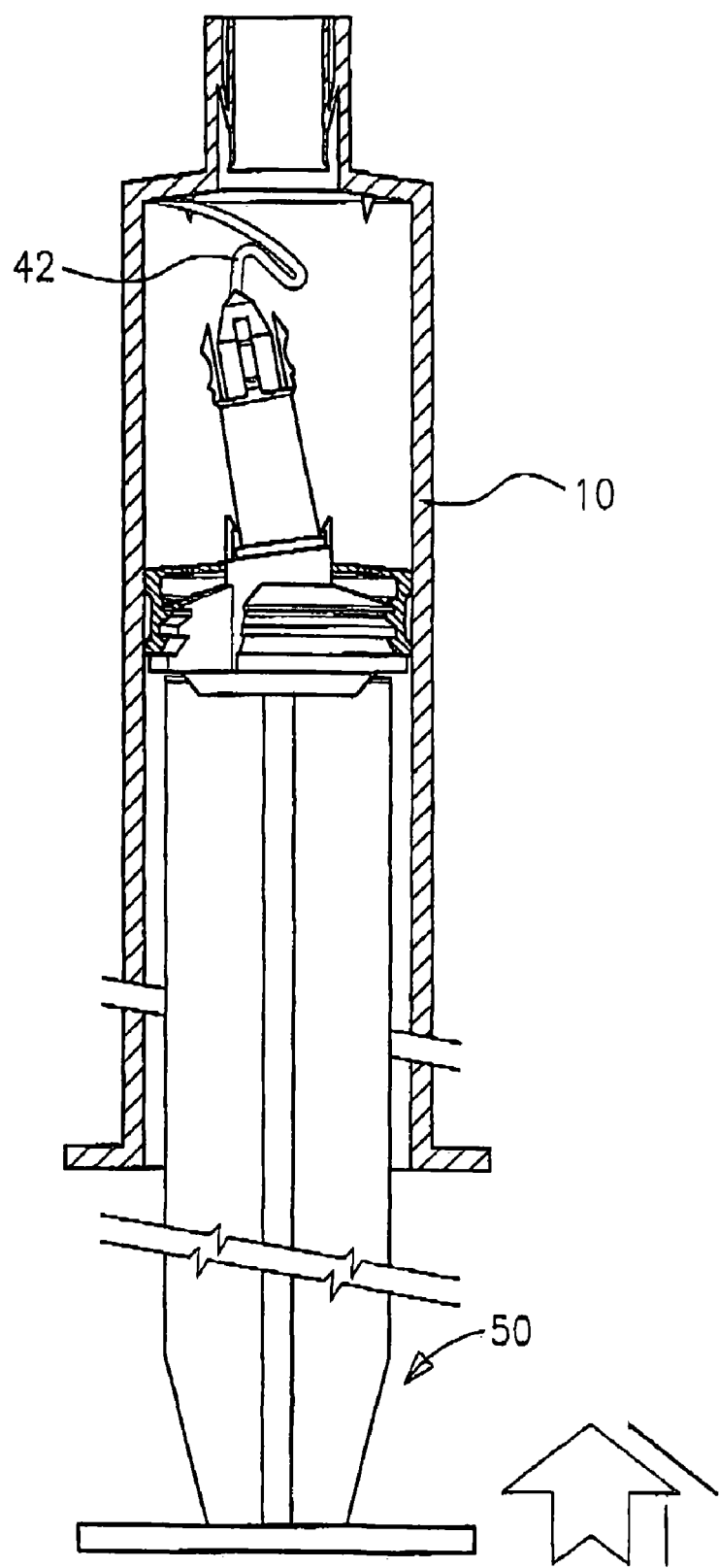

Referring to FIG. 6, displacing the plunger 50 towards the extension 12 until the piercing element 22 sticks through the piston 70 causes the flukes 62, 64 to couple with the bulge loop 34. Referring to FIG. 7, the piston 70 is pierced thereby forming a hole 76, by the piercing element 22. Referring to FIG. 1, the outside wall of fastening seat 52 has the axial channel 54. The piston 70 has the hole 76 which prevents re-use of the barrel 10 because it is broken and will leak. Referring to FIGS. 7 and 8, the flukes 62, 64 couple with the bulge loop 34 and when the plunger 50 is displaced away from extension 12, such displacement causes the channel 46 to leave the positioning spring 18 and thereby pulls the needle seat 30 into the barrel 10. Further, due to the inclined surface and the flukes 62, 64 having different heights cause the needle seat to be tilted in the barrel 10 for avoiding reuse of syringe. Refer to FIG. 9, displacing the plunger 50 towards the extension 12 after the needle seat 30 has been pulled into the barrel 10 deforms needle 42.

Figure 10:
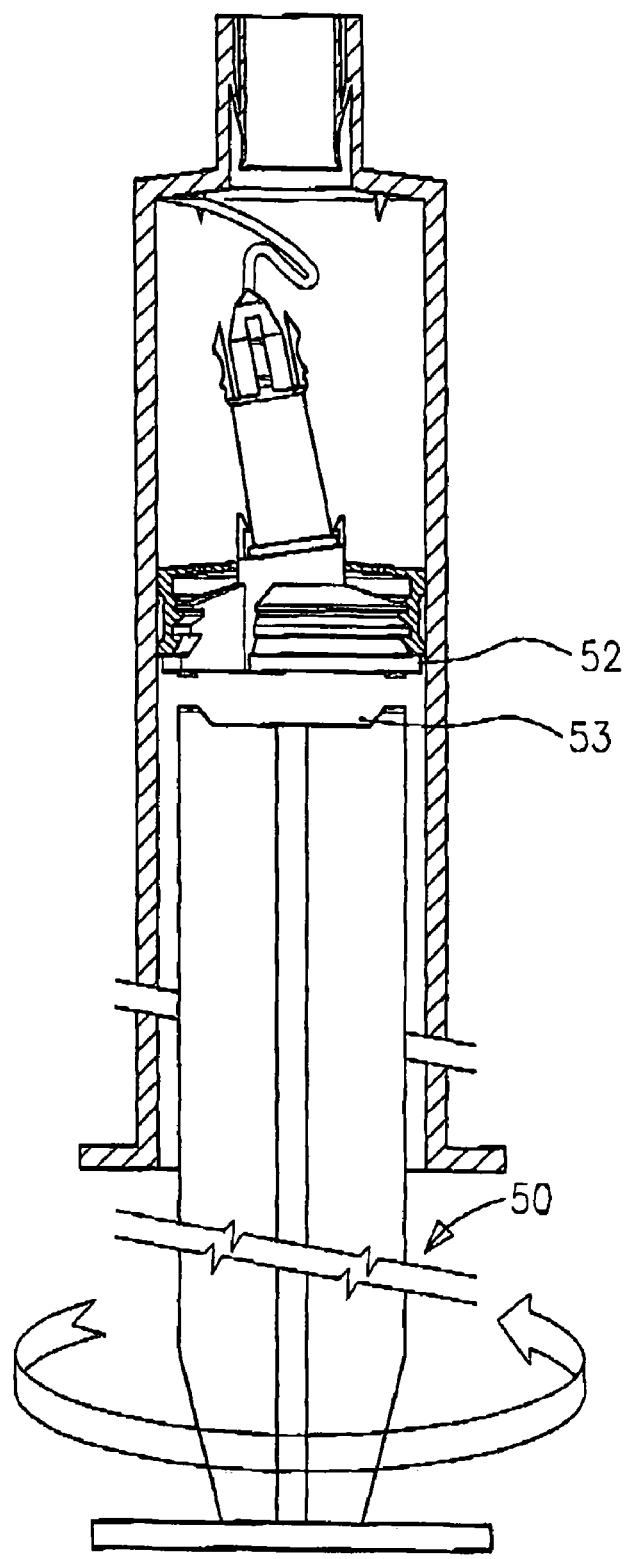

Referring to FIG. 10, the user spins the plunger 50 to break it and separate the fastening seat 52.

The injection syringe of the present invention discloses the positioning spring 18 and channel 46 of sheets 44 to fasten the needle seat 30 on the barrel 10. Using the seal spring 20 and body 32 results in excellent seal property in accordance to the spring property of seal spring 20. The spring 20 is not affected by variations in temperature. Further, after injecting, the piercing element 22 sticks the piston 70 to form the hole 76 to avoid reuse of the syringe by compromising the seal property. Also, spinning the plunger 50 to break and separate the fastening seat 52 avoids the ability to reuse the syringe.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An injection syringe with seal structure comprising:
   a hollow barrel comprising an axial extension at a top end thereof, said axial extension having a positioning spring at a top end and a seal spring at a bottom end thereof;
   a needle seat positioned inside of the axial extension and including a bulge loop at a bottom end and a needle head seat having a syringe needle at a top end thereof, said needle head seat including a plurality of positioning sheets on an outer surface thereof, said positioning sheets having channels for coupling to the positioning spring;
   a plunger placed in the hollow barrel including a fastening seat, said fastening seat having a piston, said piston including a hole for inserting a cylindrical column of the fastening seat; a top of said cylindrical column having a plurality of flukes for coupling with the bulge loop; and
   at least one piercing element formed on an inner wall of said hollow barrel, wherein said at least one piercing element pierces said piston thereby preventing re-use of the injection syringe.

2. The injection syringe with seal structure as recited in claim 1, wherein said piercing element is formed at said top end of said barrel near said bottom end of said axial extension.

3. The injection syringe with seal structure as recited in claim 1, wherein the axial extension comprises an upper channel and a lower channel thereby defining the positioning spring and the seal spring.

4. The injection syringe with seal structure as recited in claim 1, wherein an upper portion of the channel of said positioning sheet comprises a pressing channel.

5. The injection syringe with seal structure as recited in claim 1, wherein the fastening seat comprises a plurality of fastening channels at an outside thereof for coupling to a plurality of bulge rings on an inside of the piston.

6. The injection syringe with seal structure as recited in claim 1, wherein an upper surface of said cylindrical column has an inclined plane.

7. The injection syringe with seal structure as recited in claim 1, wherein a side of said fastening seat comprises an axial channel.

8. The injection syringe with seal structure as recited in claim 1, wherein a top end of said plunger includes an opening to couple to the fastening seat and to easily break the plunger after using.

9. The injection syringe with seal structure as recited in claim 1, wherein a bottom end of said plunger comprises a flange.

10. The injection syringe with seal structure as recited in claim 9, wherein said flange has an arcuate shape.

* * * * *